United States Patent [19]
Rutten et al.

[11] Patent Number: 6,083,247
[45] Date of Patent: Jul. 4, 2000

[54] PERPENDICULAR ATRIAL FIXATION/ STIMULATION LOOP

[75] Inventors: Jean J. G. Rutten, Bocholtz, Netherlands; Jaak M. O. Minten, Landen, Belgium

[73] Assignee: Medtronic, Inc., Minneapolis, Minn.

[21] Appl. No.: 09/131,902

[22] Filed: Aug. 10, 1998

[51] Int. Cl.$^7$ ........................................ A61N 1/36
[52] U.S. Cl. ................... 607/9; 607/123; 607/126; 607/128
[58] Field of Search ....................... 607/123, 122, 607/126, 128, 9

[56] References Cited

U.S. PATENT DOCUMENTS

| | | | |
|---|---|---|---|
| 4,154,247 | 5/1979 | O'Neill | 128/419 P |
| 4,317,459 | 3/1982 | Gilman | 128/785 |
| 4,497,326 | 2/1985 | Curry | 607/123 |
| 5,207,226 | 5/1993 | Bailin et al. | 128/661.08 |
| 5,431,696 | 7/1995 | Atlee, III | 607/124 |
| 5,674,274 | 10/1997 | Morgan et al. | 607/123 |
| 5,738,683 | 4/1998 | Osypka | 607/122 |
| 5,772,693 | 6/1998 | Brownlee | 607/123 |

OTHER PUBLICATIONS

U.S. application No. 08/937,510, Smits filed Sep. 22, 1997.
Brownlee, Robert R. et al., "Toward Optimizing a Preshaped Catheter and System Parameters to Achieve Single Lead DDD Pacing," *PACE*, vol. 20, May 1997, Part I, pp. 1354–1358.

*Primary Examiner*—Kennedy Schaetzle
*Attorney, Agent, or Firm*—Thomas F. Woods; Michael J. Jaro; Harold Patton

[57] ABSTRACT

The present invention provides a pacing system with a lead having a fixation element for providing stable fixation relative to the patient's SVC, preferably providing for positioning of the atrial electrodes near the sinus node. In a first embodiment, an adjustable loop is provided for engaging the inside wall of the SVC so as to obtain fixation of the lead just above the sinus node. Other embodiments utilize tine arrangements for providing the fixation relative to the SVC.

7 Claims, 5 Drawing Sheets

PERPENDICULAR ATRIAL FIXATION/STIMULATION LOOP

FIELD OF THE INVENTION

The present invention relates to the field of leads for pacing a heart, and more specifically, to leads which have an element for maintaining the positioning of the leads within the atrium.

BACKGROUND OF THE INVENTION

It has long been a desire and aim in the pacemaker art to provide a reliable single lead for use with a dual chamber pacing system. As is known, in the past a conventional dual chamber system typically has utilized two leads which interconnect the implanted pacemaker with the ventricle and atrium, respectively. Thus, in such a system a ventricular lead interconnects the pacemaker with the ventricle, delivering ventricular pace pulses to the ventricle and sensing ventricular conduction activity and returning such sensed signals to the pacemaker. A second, atrial lead is provided for performing the same functions with respect to the atrium. A long recognized disadvantage of this arrangement is the need to provide two leads, which adds to expense and increases reliability problems; and also takes significantly more physician time in placing the two leads at time of implantation.

The VDD or VDD(R) single pass lead provides a response to the two-lead problem, and has been in use for some time. In such a single lead construction, the distal tip has a fixation mechanism for fixing to the apex of the ventricle, while the lead is essentially "floating" or unattached in the atrium. The VDD lead is provided with one or two atrial electrodes, typically ring electrodes which are positioned in the atrium, for sensing P wave signals, thereby providing the ability to time out an AV delay and provide ventricular pace pulses which are synchronized to sensed atrial depolarizations. While some attempts have been made to pace from floating atrial electrodes, this has generally been ineffectual.

A further advance is what is known as the DDD lead, which has enhancements which aim to provide more stable contact with the atrial wall, so as to enable more reliable atrial pacing as well as reliable atrial sensing. The DDD lead typically includes features added to the lead portion to enable DDD operation, i.e., pacing and sensing in both chambers. The additional features are intended to maintain the atrial electrodes closer to the atrial wall when the distal tip is anchored to the ventricular apex. These features may include, for example, an atrial tine, or small extension from the lead body, which may be designed to provide better fixation against the atrial wall. The atrial tine may also be provided with a distal electrode, for making direct contact with the atrial wall. Other features which have been adapted to DDD-type leads include a variety of S-shaped leads and pre-shaped sections, for the purpose of providing more stable atrial positioning. See, for example, U.S. Pat. No. 5,628,778, Kruse; and U.S. Pat. No. 4,154,247, O'Neill; and "Towards Optimizing a Pre-Shaped Catheter and System Parameters to Achieve Single Lead DDD Pacing," PACE, Vol.20, May 1997, Part I.

Another problem that arises with a single DDD lead is that of maintaining the pace/sense lead area in a stable location, preferably not far away from the sinus node. While atrial tines provide some improvement in this regard, it is difficult with an atrial tine to provide accurate positioning relative to the sinus node. There remains a need to improve the design of a lead so as to provide an improved ability to adjustably fix the lead at or near the opening of the superior vena cava (SVC) into the atrium, so as to hold the atrial electrode (or electrodes) proximate to the sinus node, thereby avoiding a long substrate delay.

SUMMARY OF THE INVENTION

In accordance with the above, the present invention is directed to a cardiac pacing system which incorporates a pacing lead having a fixation means for fixing a portion of the lead with respect to the patient's SVC. The pacing lead of the present invention has a distal end and a proximal end, and a lead body extending therebetween. The lead further has a ventricular electrode positioned at about the distal end of the lead, and a conductor extending within the lead body through a lumen from the proximal end to the ventricular electrode. The lead also has an element for fixing a portion of the lead with respect to the patient's SVC, which may also serve to stimulate the heart. The fixation/stimulation element is positioned on the lead at about 12 cm to 19 cm from the distal end of the lead so that when the distal end is positioned in the patient's right ventricular apex, the fixation/stimulation element is positioned in the SVC.

The fixation/stimulation element suitably is a conductor coil which forms a fixation loop which is extendable laterally from the lead body so as to contact the inside wall of the SVC and serves to anchor the lead. The loop is preferably completely covered with a non-conductive material or can have an exposed portion which has a surface area which can serve as an electrode. A ring electrode can also be positioned proximate to the fixation loop. A manipulation element is provided at the proximal end of the lead to enable extension and retraction of the conductor coil, so as to adjust the loop between engaging and non-engaging states. Thus, the coil may be extended through a lumen into the lead body from the proximal end such that it opens into a lateral loop for engaging the SVC, and when the coil is retracted, the loop is withdrawn around the lead body. In other embodiments of the invention, the fixation/stimulation element is a three-pronged tine or a two-pronged tine, adapted to engage the inner wall of the SVC.

DESCRIPTION OF THE PREFERRED EMBODIMENTS

Applicant's invention provides a pacing lead with a fixation/stimulation element for providing stable fixation of the atrial electrodes near the sinus node. The fixation/ stimulation element fixes a portion of the lead with respect to the patient's SVC so that when the distal end of the lead is positioned in the patient's right ventricular apex, the fixation/stimulation element is positioned in the patient's SVC. Thus, as the heart contracts, the fixation/stimulation element maintains positioning of the atrial portion of the lead, which contains atrial electrodes, such that the atrial electrodes maintain substantial contact with the atrial wall.

Figure 1:
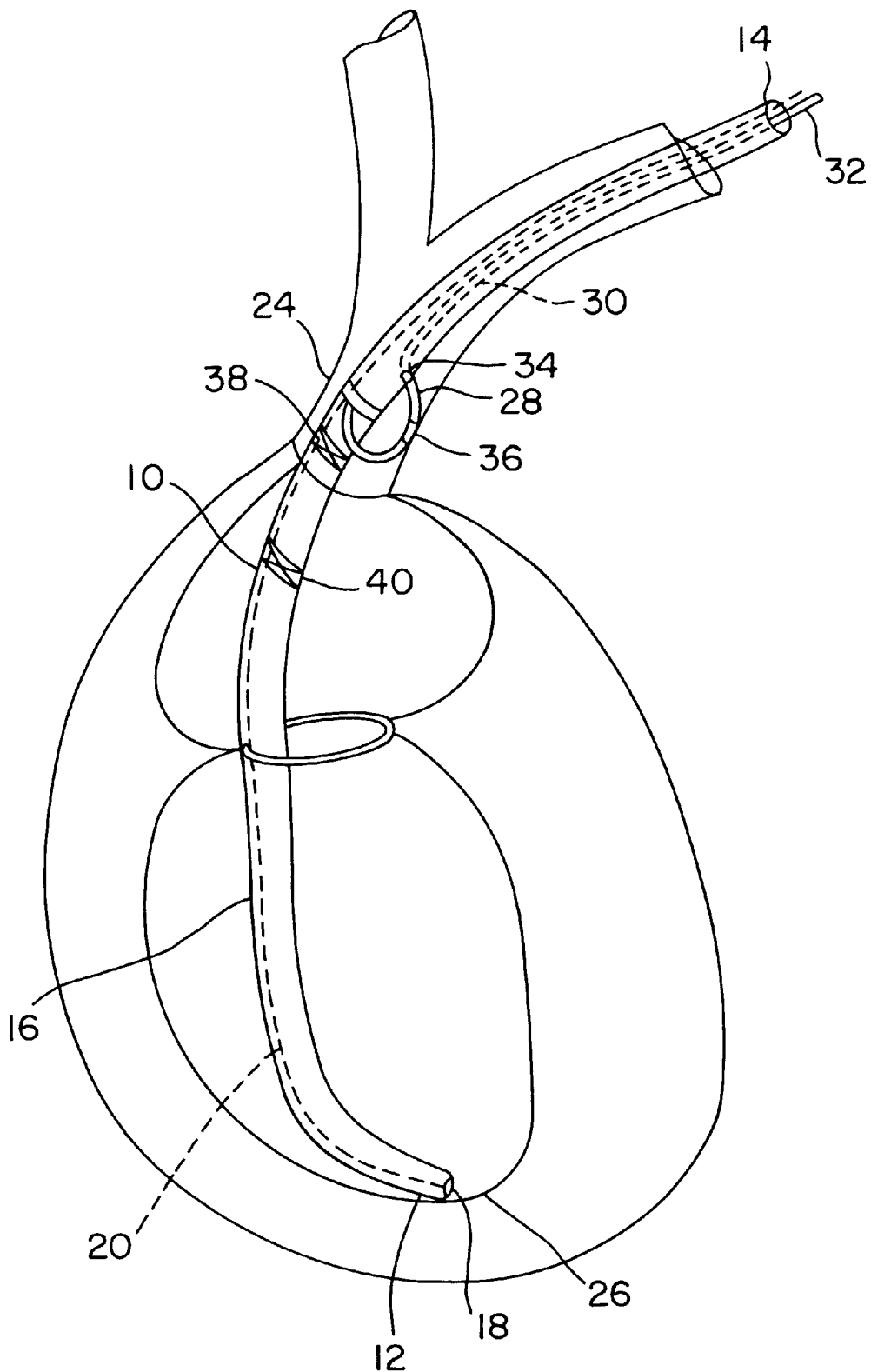
FIG. 1 is an illustrative representation of a preferred pacing lead positioned within a patient's heart having a fixation loop which engages the patient's SVC.
Figure 5:
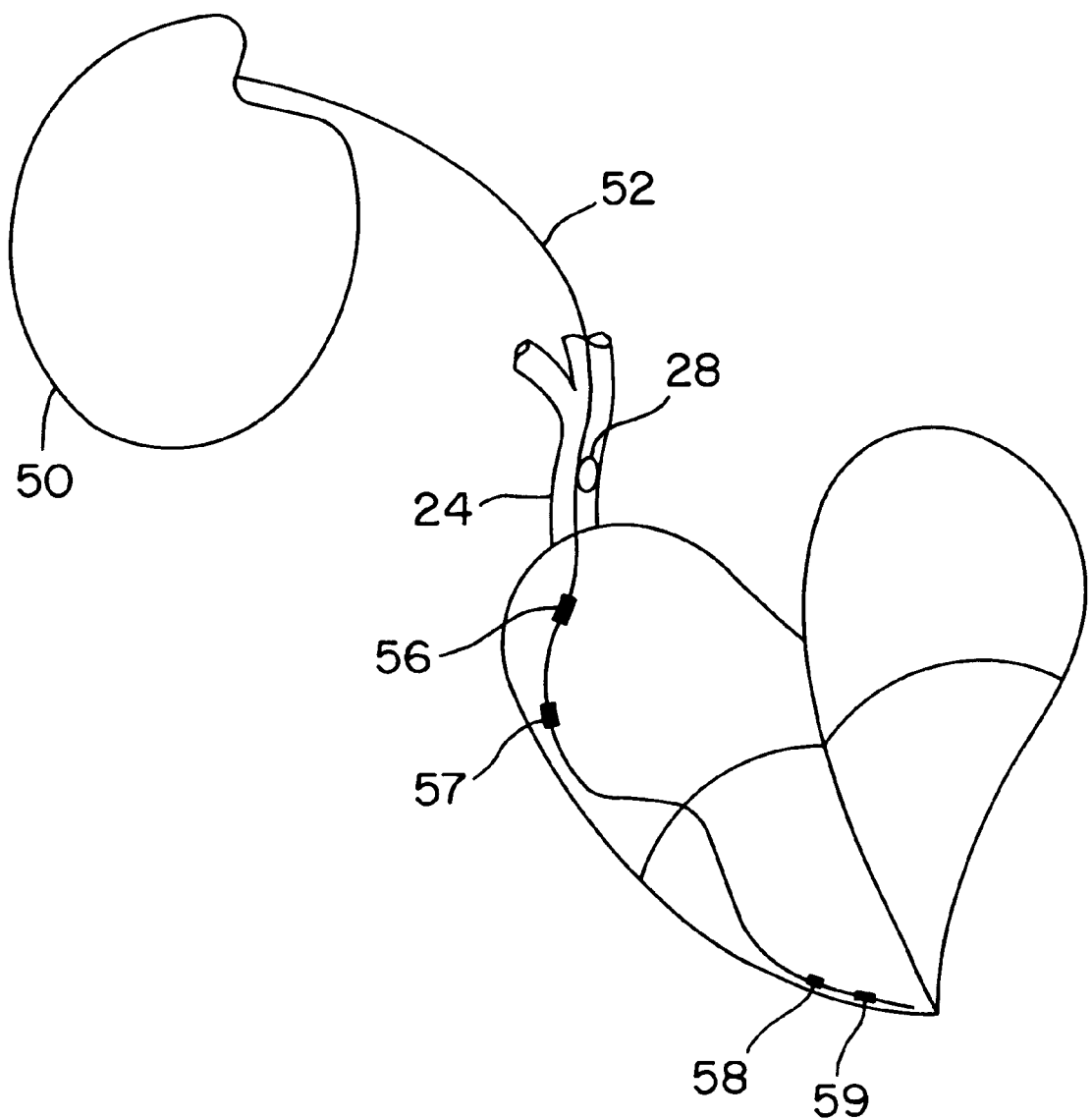
FIG. 5 is a diagrammatic sketch of a preferred system for pacing a patient's heart in which the lead has a fixation loop engaging the SVC.

Referring now to FIG. 1, there is shown an illustrative embodiment of a preferred pacing lead having a fixation/ stimulation element positioned within a patient's SVC. The implantable pacing lead 10 for pacing a patient's heart has a proximal end 14 and a distal end 12. The proximal end is connectable to a pacemaker 50, as illustrated in FIG. 5. The distal end is positioned in the right ventricular apex 26 of the heart. A lead body 16 extends between the distal and proximal ends of the lead. The lead body is preferably made of non-conductive or insulative materials which are widely known to those skilled in the art of implantable leads. In addition, the lead body is preferably between about 1.0 and 4.0 mm in diameter, and more preferably between about 2.0 and 2.5 mm in diameter.

Still referring to FIG. 1, a preferred lead has a ventricular electrode 18 which is positioned at about the distal end of the lead. The electrode is made of conductive materials which are well known to those skilled in the art of pacing leads. Preferably, the electrode is made of platina. The ventricular electrode may be a standard tip electrode known to those skilled in the art of leads or may be a ring electrode. Preferably, the ventricular electrode is positioned at about the distal end of the lead. A ventricular conductor 20 is within a lumen inside the lead body and connects the proximal end of the lead to the ventricular electrode. In preferred embodiments of the invention, the lead has two electrodes, e.g., one tip electrode and one ring electrode, or two ring electrodes. Of course, an embodiment of the invention contemplates a unipolar arrangement, using just one ventricular electrode, and using the pacemaker as the other reference electrode.

Still referring to FIG. 1, a preferred lead also has a fixation/stimulation element for fixing a portion of the lead with respect to the patient's SVC 24. The fixation/ stimulation element is positioned on the lead about 12 cm to 19 cm from the distal end of the lead, so that when the distal end of the lead is positioned in the patient's right ventricular apex, the fixation/stimulation element is positioned in the SVC.

Figure 2:
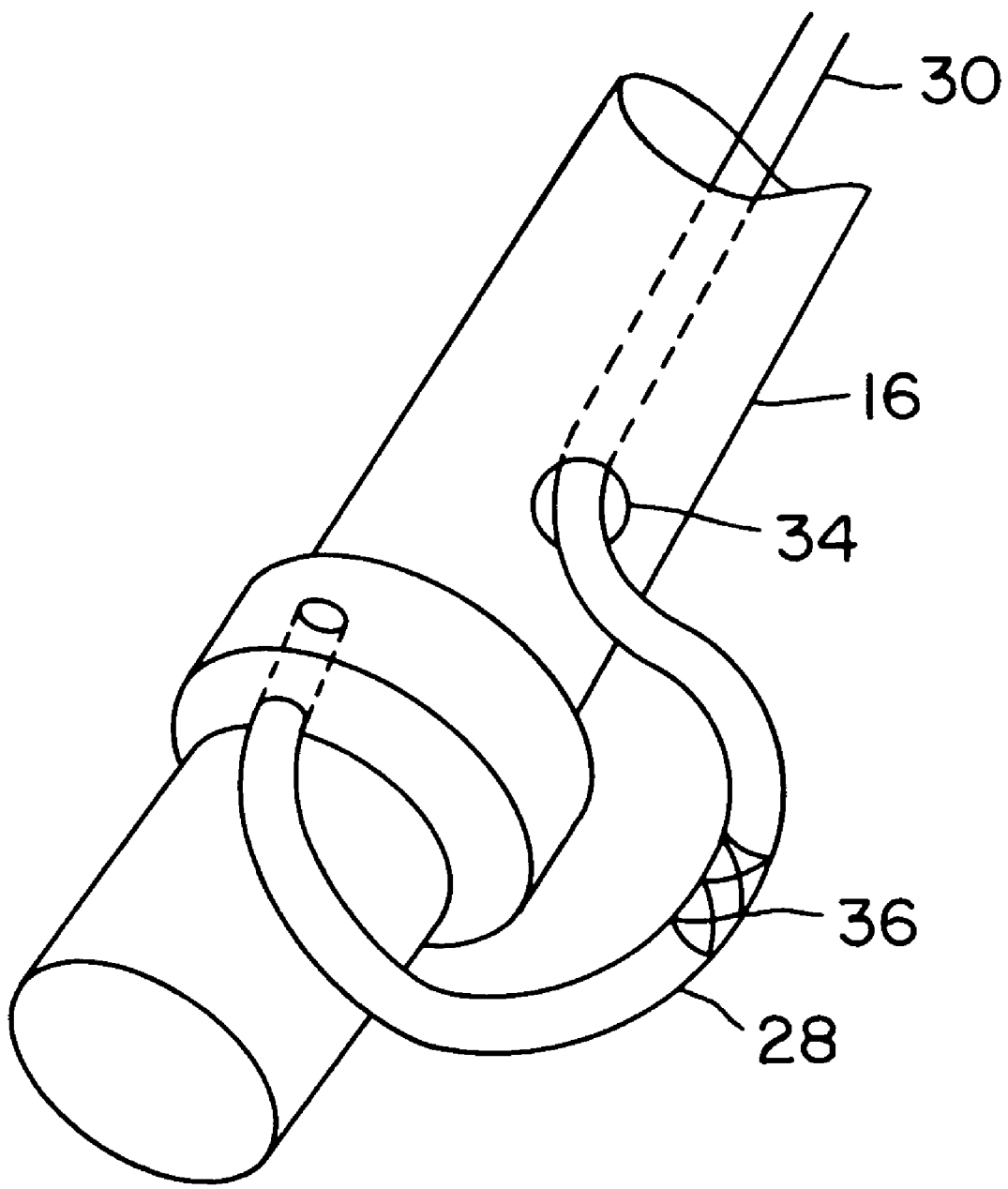
FIG. 2 is an illustrative representation of a first embodiment of a fixation-stimulation element for positioning within the SVC in accordance with this invention.

In a preferred embodiment of the invention, as depicted in FIG. 1, the fixation/stimulation element is an extendable conductor coil 30 which extends through a lumen in the lead from the proximal end of the lead to a portion of the lead which is positioned within the SVC. The conductor coil forms a fixation loop 28 outside the lead body whereby the loop contacts the inside wall of the SVC when fully extended. Referring now to FIG. 2, there is shown a more detailed illustration of the fixation/stimulation element shown in FIG. 1. The extendable conductor coil extends from the proximal end of the lead through an opening 34 in the lead body at the portion of the lead which is positioned within the SVC. The conductor coil forms the fixation loop external to the lead body. The size of the fixation loop when fully extended is from about 2 cm to about 4 cm in length along the axis of the lead body and has a radius of 1 to 2 cm from the lead body.

The total diameter of the lead body and extended fixation loop is about 1.5 to about 2.5 cm. The distal end of the conductor coil is secured to the lead body near the opening, such that when the coil is extended into the lead body from the proximal end, it opens into a lateral loop for engaging the SVC, and when the coil is retracted, the loop is withdrawn around the lead body.

In preferred embodiments, a portion or all of the fixation loop is enclosed within non-conductive or insulative materials. In some embodiments of the invention, at least a portion of the fixation loop surface is exposed and serves as an electrode 36 with a surface area of about 4 to 30 mm$^2$, more preferably about 8 mm$^2$. The fixation/stimulation element can be used in tachycardia as well as bradycardia applications. In addition, the fixation loop can be used for both pace and sense applications and can also be used for atrial defibrillation, particularly when the electrode surface area is large, i.e., about 30 mm$^2$.

Referring back to FIG. 1, there is shown a lead in which the conductor coil is connected to a manipulation element at the proximal end of the lead for extending and retracting the extendable coil. The manipulation element also preferably locks the extendable coil conductor in various positions such that the coil can no longer be extended or retracted. As depicted in FIG. 1, a preferred manipulation element includes, for example, grip element 32. In addition, the manipulation element can also be a connector leg, which is well known to those skilled in the art. Once the conductor coil has been fully extended and the fixation loop engages the SVC in a perpendicular manner, the grip element can be adjusted or locked such that the fixation loop cannot be disengaged from the SVC by retracting the conductor coil. In addition, after the lead is introduced into the patient, the conductor coil is pulled out, so that the loop hugs the lead body.

In other preferred embodiments of the invention, as depicted in FIG. 1, the lead also has a ring electrode 38 adjacent the fixation loop, for pacing in the vicinity of the SVC. In other embodiments of the invention, the lead also has an atrial ring electrode 40 which is positioned in the atrium. The atrial ring electrode is positioned in the portion of the lead which is distal to the fixation loop. In other embodiments of the invention, the lead may have two ring electrodes, one suitably positioned to be in the SVC and one positioned on the lead so as to be in the atrium, as illustrated in FIG. 1. In other embodiments of the invention, the atrium may be defibrillated using the fixation loop.

The above-described lead can be inserted into the SVC and into the heart such that the distal end of the lead engages the ventricular apex. During insertion of the lead, preferably with an introducer sheath or stylet, the coil is retracted such that the loop is substantially lateral to the lead body. Once the distal end is engaged, the conductor coil is extended resulting in formation of the fixation loop. The conductor coil can be extended to fit the SVC diameter of the particular patient. In addition, the fixation loop can engage the inner wall of the SVC at any angle desired. Thus, the loop need not be, but preferably is, extended to fixate perpendicular to the wall of the SVC. In addition, the position of the loop can be altered so as to optimally be positioned for sending and/or receiving atrial signals.

Figure 3:
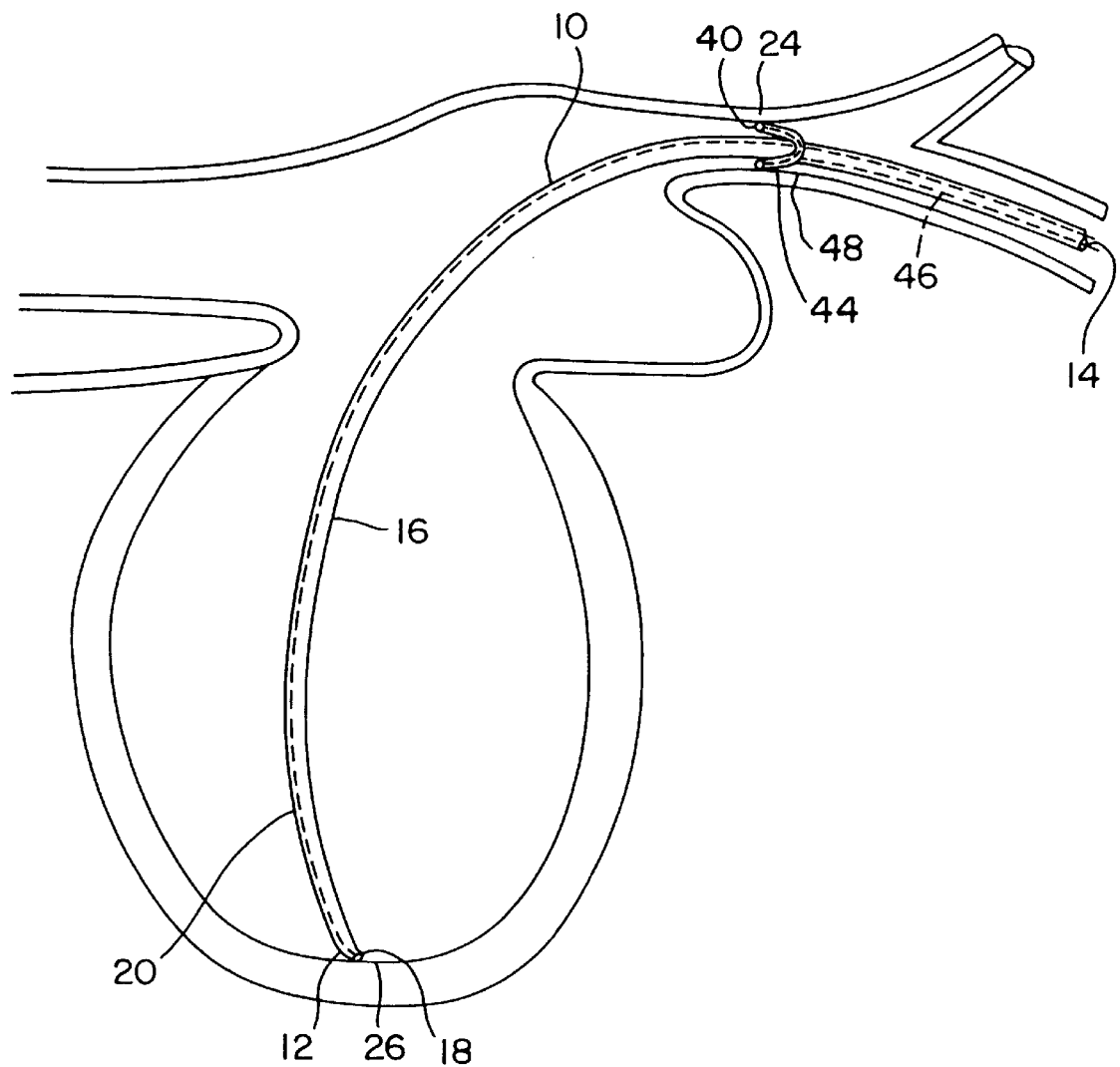
FIG. 3 is an illustrative representation of another embodiment of a pacing lead in accordance with this invention, having a two-pronged tine positioned for fixation in the patient's SVC.

Referring now to FIG. 3, there is shown another preferred embodiment wherein the fixation/stimulation element of the lead is a two-pronged tine 48. The two-pronged tine is positioned on the lead such that when the distal end of the lead is engaged with the ventricular apex, the portion of the lead comprising the two-pronged tine engages the inner wall of the SVC. Preferably, the two-pronged tine is positioned from about 12 cm to about 19 cm from the distal end of the lead. Each prong is preferably about 15 mm to about 20 mm in length and preferably has an outer diameter of about 1.5 mm to about 2.0 mm. The tine is preferably made of a flexible material, such as, for example, silicone rubber. The lead may also have an electrode 40 positioned at about the distal end 44 of one or both of the two prongs so as to suitably contact the inner wall of the SVC, and a second conductor 46 extending within a lumen within one or both of the two prongs from the proximal end of the lead to the electrodes. The electrode may be either a tip electrode or ring electrode, as described above. Although FIG. 3 depicts the two-pronged tine in an orientation such that the distal ends of the tines point towards the distal end of the lead, the present invention also contemplates a two-pronged tine in an orientation such that the distal ends of the tines point towards the proximal end of the lead.

Figure 4A:
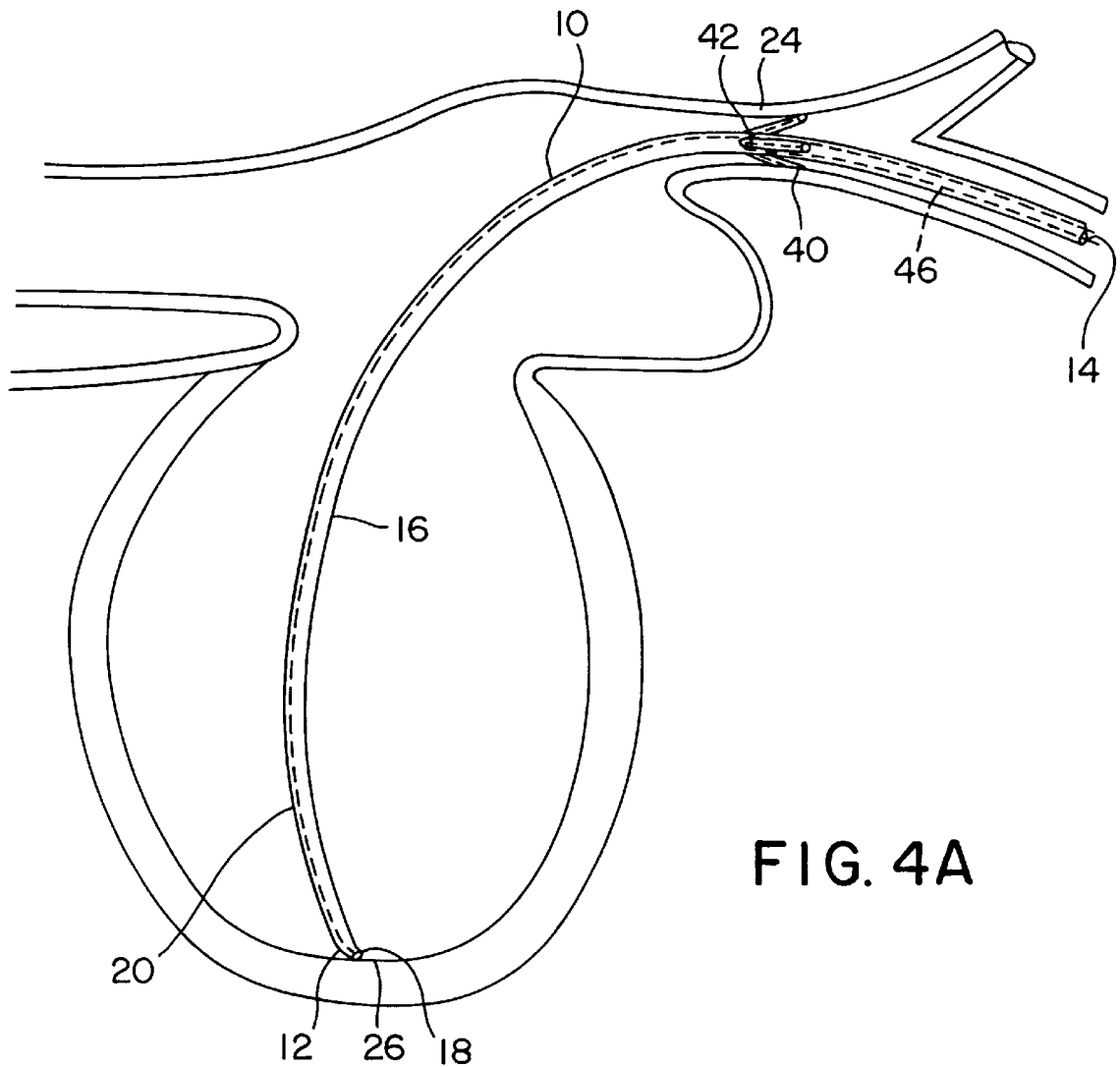
FIG. 4A is an illustrative representation of another embodiment of a pacing lead in accordance with this invention, having a three-pronged tine positioned for fixation in the patient's SVC.
Figure 4B:
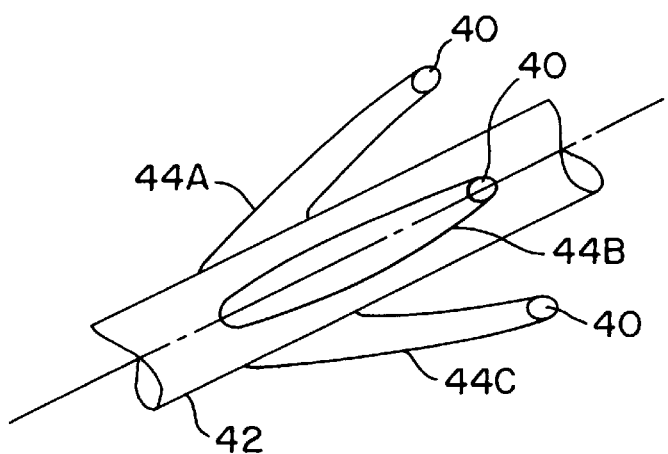
FIG. 4B is an illustrative representation of a three-pronged tine.

Referring now to FIG. 4A, there is shown another preferred embodiment wherein the fixation/stimulation element of the lead is a three-pronged tine 42. The three-pronged tine is positioned on the lead such that when the distal end of the lead is engaged with the ventricular apex, the portion of the lead having the three-pronged tine engages the inner wall of the SVC. Preferably, the three-pronged tine is positioned from about 12 cm to about 19 cm from the distal end of the lead. Referring now to FIG. 4B, shown is a three-pronged tine. Each prong 44A, 44B, and 44C is preferably about 15 mm to about 20 mm in length and preferably has an outer diameter of about 1.5 mm to about 2.0 mm. The tine is preferably made of a flexible material, such as, for example, silicone rubber. In other embodiments of the invention, the lead also has an electrode 40 positioned at about the distal end of one, two or all of the three prongs, and a second conductor 46 extending within a lumen within one, two or all of the three prongs from the proximal end of the lead to the electrodes. The electrode may be either a tip electrode or ring electrode, as described above. Although FIG. 4A depicts the three-pronged tine in an orientation such that the distal ends of the tines point towards the distal end of the lead, the present invention also contemplates a three-pronged tine in an orientation such that the distal ends of the tines point towards the proximal end of the lead.

It is to be understood that the present invention contemplates many types of fixation/stimulation elements not depicted in the Figures, including, for example, an umbrella-like configuration in which the fixation/stimulation element expands outwardly to engage the inner wall of the SVC upon manipulation of the lead. In addition, the umbrella-like fixation/stimulation element may also have at least one electrode as described above for the other depicted embodiments.

The leads of the present invention can be positioned in the patient's heart by using introducer sheaths or stylets, which are well known to those skilled in the art of leads. In addition, an anchoring sleeve may be used to fix the lead near its proximal end to a rib or some element in the pocket in order to prevent shifting of the pacemaker in a pocket from affecting the lead position in the heart. In addition, an advantage of using a lead without any atrial tines is that the practitioner can insert the lead into the heart using a smaller diameter introducer.

Referring now to FIG. 5, shown is a diagrammatic sketch of a pacing system in accordance with this invention. Pacemaker 50 is a standard DDD-type pacemaker, meaning that it has two pulse channels for delivering pacing pulses to the atrium and ventricle respectively. The pacemaker also has sensing channels for sensing and processing spontaneous signals from the atrium (via P waves) and ventricle (via R waves and T waves). The pacemaker may, of course, be a variation of a DDD-type, e.g., a DDD(R), or it can be a 4 chamber pacemaker which also has channels for pacing the left atrium and the left ventricle. As shown, pacemaker 50 is connected to the patient's heart by means of a lead 52, which is one of the above-described embodiments. The lead has a fixation loop 28 which engages the inner wall of the SVC. Of course, the pacing systems in accordance with the invention may also have other fixation/stimulation elements such as those described above. Atrial electrodes 56 and 57 provide delivery of pace pulses to the atrium, and sense spontaneous P waves. The atrial electrodes can be any of the electrodes described above. Ventricular electrodes 58 and 59 provide delivery of pace pulses to the ventricle and sense R waves for transmission back to the pacemaker. The ventricular electrodes can be any of the electrodes described above. Of course, a unipolar configuration could also be used in either or both chambers of the heart, in which case only one electrode would be necessary per chamber, the pacemaker being used as the other electrode.

What is claimed is:

1. A pacing lead for pacing a patient's heart, said lead comprising:

a distal end and a proximal end, and a lead body extending therebetween;

a ventricular electrode positioned at about said distal end, and a ventricular conductor extending within said lead body from said proximal end to said ventricular electrode; and fixation means for fixing a portion of said lead with respect to the patient's superior vena cava, positioned on said lead at about 12 cm to 19 cm from said distal end, so that when said distal end is positioned in the patient's right ventricular apex said fixation means is positioned in said superior vena cava; wherein said fixation means comprises an extendable conductor coil forming a fixation loop which extends substantially laterally to said lead body, whereby said loop contacts the inside wall of said superior vena cava, wherein said fixation means further comprises manipulation means at said proximal end, for extending and retractsn said extendable coil:

wherein said lead has an opening in said lead body, and said extendable coil comes out of said opening, the end of said coil being secured to said lead body near said opening, whereby when said coil is extended into said lead body from said proximal end, it opens into a lateral fixation loop for engaging the superior vena cava, and when said coil is retracted, said loop is withdrawn around said lead body.

2. The lead as described in claim 1, wherein said fixation loop has a surface, at least a portion of which is exposed, whereby said portion is an electrode.

3. The lead as described in claim 2, said lead having a ring electrode adjacent said fixation means.

4. The lead as described in claim 2, said lead having a ring electrode which is positioned distal to said fixation means so as to be in the atrium when said fixation means engages the SVC.

5. The lead as described in claim 1, said lead comprising two ring electrodes which are positioned distal to said fixation means so as to be in the atrium when said fixation means engages the SVC.

6. A system for pacing a patient's heart, comprising:

a pacemaker; and a pacing lead for pacing a patient's heart, said lead comprising:

a distal end and a proximal end, and a lead body extending therebetween;

a ventricular electrode positioned at about said distal end, and a ventricular conductor extending within said lead body from said proximal end to said ventricular electrode; and fixation means for fixing a portion of said lead with respect to the patient's superior vena cava, positioned on said lead at about 12 cm to 19 cm from said distal end, so that when said distal end is positioned in the patient's right ventricular apex said fixation means is positioned in said superior vena cava; wherein said fixation means comprises an extendable conductor coil forming a fixation loop which extends substantially laterally to said lead body, whereby said loop contacts the inside wall of said superior vena cava;

wherein said lead has an opening in said lead body, and said extendable coil comes out of said opening, the end of said coil being secured to said lead body near said opening, whereby when said coil is extended into said lead body from said proximal end, it opens into a lateral fixation loop for engaging the superior vena cava, and when said coil is retracted, said loop is withdrawn around said lead body.

7. The system as described in claim 6, wherein said fixation loop has a surface, at least a portion of which is exposed, whereby said portion is an electrode.

* * * * *

UNITED STATES PATENT AND TRADEMARK OFFICE
CERTIFICATE OF CORRECTION

PATENT NO. : 6,083,247
DATED : July 4, 2000
INVENTOR(S) : Rutten et al.

It is certified that error appears in the above-identified patent and that said Letters Patent is hereby corrected as shown below:

Column 6,
Line 41, change "for extending and retractsn" to -- for extending and retracting --.

Signed and Sealed this

Eighteenth Day of March, 2003

JAMES E. ROGAN
*Director of the United States Patent and Trademark Office*